United States Patent [19]
Bishop et al.

[11] Patent Number: 6,166,000
[45] Date of Patent: Dec. 26, 2000

[54] METHODS FOR PREPARATION AND USE OF 1α, 24(S)-DIHYDROXY VITAMIN D$_2$

[75] Inventors: Charles W. Bishop, Verona, Wis.; Glenville Jones, Kingston, Canada; Joyce C. Knutson, Madison, Wis.; Stephen Strugnell, Kingston, Canada

[73] Assignee: Bone Care International, Inc., Madison, Wis.

[21] Appl. No.: 08/472,499

[22] Filed: Jun. 7, 1995

Related U.S. Application Data

[62] Division of application No. 08/275,641, Jul. 14, 1994, abandoned, which is a continuation of application No. 07/940,246, filed as application No. PCT/US92/00313, Jan. 7, 1992, abandoned, which is a continuation-in-part of application No. 07/637,867, Jan. 8, 1991, abandoned.

[51] Int. Cl.$^7$ .......................... A61K 31/59; C07C 401/00
[52] U.S. Cl. .................................. 514/167; 552/653
[58] Field of Search .............................. 552/653; 514/167

[56] References Cited

U.S. PATENT DOCUMENTS

| | | |
|---|---|---|
| 3,880,894 | 4/1975 | DeLuca et al. . |
| 4,022,891 | 5/1977 | Takeshita et al. . |
| 4,159,326 | 6/1979 | Barton et al. . |
| 4,195,027 | 3/1980 | DeLuca et al. . |
| 4,338,250 | 7/1982 | DeLuca et al. . |
| 4,670,190 | 6/1987 | Hesse et al. . |
| 4,719,205 | 1/1988 | DeLuca et al. . |
| 4,866,048 | 9/1989 | Calverley et al. ....................... 514/167 |
| 4,960,716 | 10/1990 | Harvey et al. ........................... 436/542 |
| 4,973,721 | 11/1990 | Ikekawa et al. ........................ 552/653 |
| 5,093,519 | 3/1992 | Bouillon et al. ........................ 560/194 |
| 5,098,899 | 3/1992 | Gilbert et al. . |
| 5,232,836 | 8/1993 | Bouillon et al. ............................. 435/8 |
| 5,242,824 | 9/1993 | Hellstrom et al. ................. 435/240.27 |
| 5,401,731 | 3/1995 | Calverley et al. ....................... 514/167 |
| 5,763,428 | 6/1998 | Knutson et al. ......................... 514/167 |

OTHER PUBLICATIONS

Shieh et al., "Evaluation of the cytotoxic mechanisms mediated by the broad–spectrum antitumor alkaloid acronycine and selected semisynthetic derivatives". Chem. Biol. Interact. vol. 81, 35–55, 1992.

R. Belsey, H. F. DeLuca and J. T. Potts, Jr., *Rapid Communications*, pp. 554–557 (1971).

E. G. Bligh and W. J. Dyer, *Canadian Journal of Biochemistry and Physiology*, vol. 37, pp. 911–917 (1959).

H. F. DeLuca and V. K. Ostrem, *Prog. Clin. Biol. Res.*, vol. 259, pp. 41–55 (1988).

M. F. Holick, A. Kleiner–Bossallier, H. K. Schnoes, P. M. Kasten, I. T. Boyle and H. F. DeLuca, *J. Biol. Chem.*, vol. 248, pp. 6691–6696 (1973).

B. W. Hollis, *Clin. Chem.*, vol. 32, No. 11, pp. 2060–2063 (1986).

R. L. Horst, N. J. Koszewski and T. A. Reinhardt, *Biochem.*, vol. 29, pp. 578–582 (1990).

S. Ishizuka, K. Bannai, T. Naruchi and Y. Hashimoto, *Steroids*, vol. 37, No. 1, pp. 33–42 (1981).

S. Ishizuka, K. Bannai, T. Naruchi and Y. Hashimoto, *Steroids*, vol. 39, No. 1, pp. 53–62 (1982).

G. Jones, *Clin. Chem.*, vol. 24, No. 2, pp. 287–298 (1978).

G. Jones, A. Rosenthal, D. Segev, Y. Mazur, F. Frolow, Y. Halfon, D. Rabinovich, and Z. Shakked, *Biochemistry*, vol. 18, No. 6, pp. 1094–1101 (1979).

G. Jones, H. K. Schnoes, L. Levan and H. F. DeLuca, *Archives of Biochemistry and Biophysics*, vol. 202, No. 2, pp. 450–457 (1980).

H. E. Paaren, H. F. DeLuca and H. K. Schnoes, *J. Org. Chem.*, vol. 45, pp. 3253–3258 (1980).

J. G. Rheinwald and H. Green, *Cell*, vol. 6, pp. 331–343 (1975).

H. L. Shieh, J. M. Pezzuto and G. A. Cordell, *Chem.–Biol. Interact.*, vol. 81, pp. 35–55 (1992).

S. Strugnell, M. J. Calverley and G. Jones, *Biochemical Pharmacology*, vol. 40, pp. 333–341 (1990).

S. Tam, S. Strugnell, R. G. Deeley and G. Jones, *Journal of Lipid Research*, vol. 29, pp. 1637–1642 (1988).

Calcium Regulation and Bone Metabolism Basic and Clinical Aspects, vol. 9 in R. L. Horst, N. A. Koszewski and T. A. Reinhardt,*Quantitation and Biological Evaluation of the C–24 Hydroxylation Pathway of Vitamin D$_2$*, Excerpta Medica, Amsterdam–New York–Oxford, p. 598, 1987.

*Analytical Biochemistry*, vol. 162, 1987, N. J. Koszewski, T. A. Reinhardt, D. C. Beitz, J. L. Napoli, E. G. Baggiolini, M. R. Uskokovic, and R. L. Horst, "Use of Fourier Transform $^1$H NMR in the Identification of Vitamin D$_2$Metabolites", pp. 446–452.

*Archives of Biochemistry and Biophysics*, vol. 270, No. 2, May 1, 1989, G. W. Engstrom and N. J. Koszewski, "Metabolism of Vitamin D$_2$ in Pig Liver Homogenates: Evidence for a Free Radical Reaction", pp. 432–440.

*Biochemistry*, vol. 29, No. 4, 1990, G. S. Reddy and K. Tserng, "24,25,28–Trihydroxyvitamin D$_2$and 24,25,26–Trihydroxyvitamin D$_2$: Novel Metabolites of Vitamin D$_2$", pp. 943–949.

*Primary Examiner*—Barbara Badio
*Attorney, Agent, or Firm*—Michael Best & Friedrich LLP

[57] ABSTRACT

1α,24(S)-Dihydroxy vitamin D$_2$ which is useful as an active compound of pharmaceutical compositions for the treatment of disorders of calcium metabolism and for various skin disorders. The invention also includes preparation of synthetic 1α,24(S)-dihydroxy vitamin D$_2$ starting from ergosterol which is converted in six steps to 24-hydroxyergosterol. 24-Hydroxyergosterol is irradiated and thermally converted to 24-hydroxy vitamin D$_2$ which is converted in six steps to 1α,24(S)-dihydroxy vitamin D$_2$. The syntheses also produced novel intermediates.

10 Claims, 4 Drawing Sheets

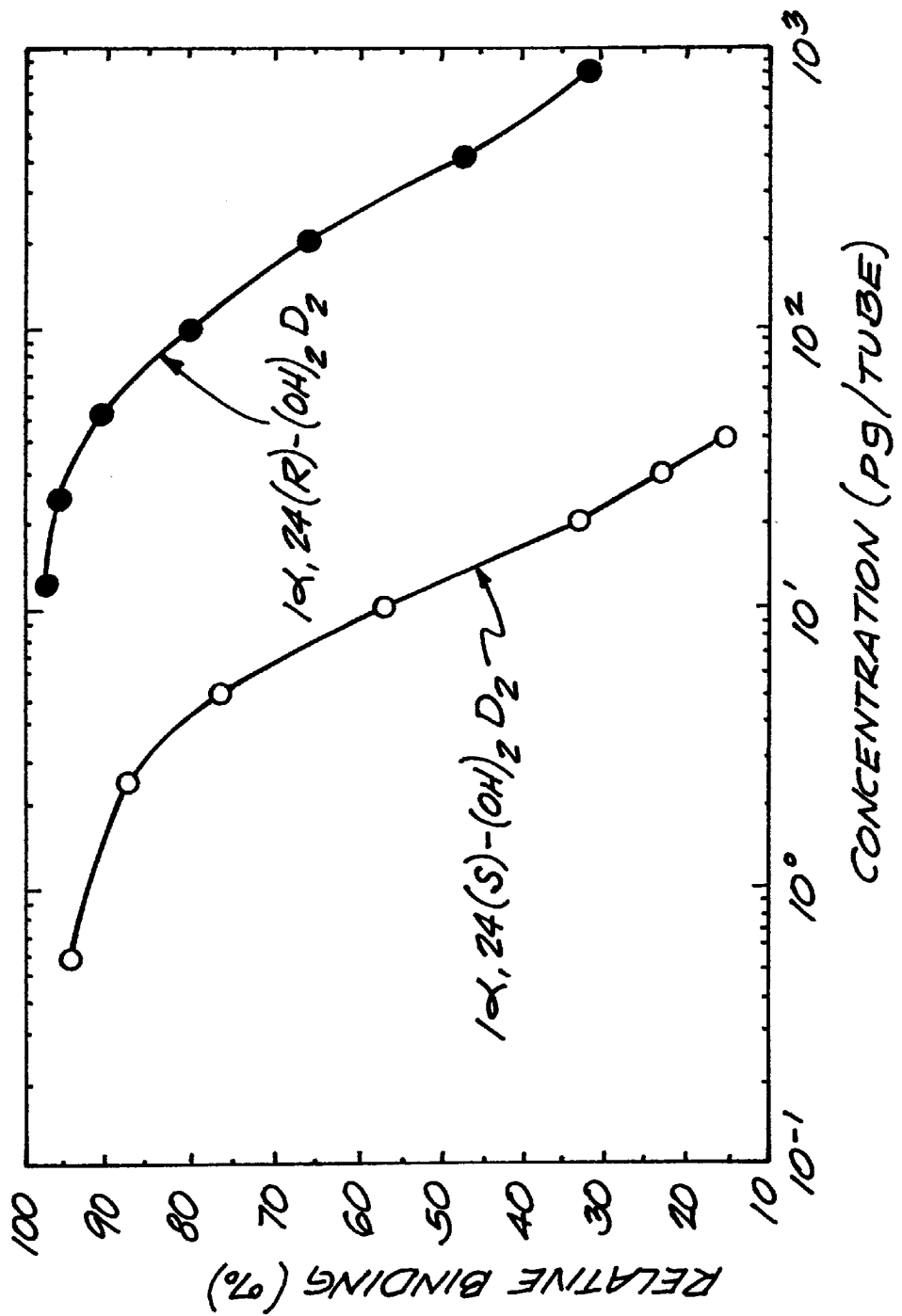

METHODS FOR PREPARATION AND USE OF 1α, 24(S)-DIHYDROXY VITAMIN $D_2$

This is a division of application Ser. No. 08/275,641, filed Jul. 14, 1994, now abandoned, which is a continuation of application Ser. No. 07/940,246, filed Aug. 28, 1992, now abandoned, which is a continuation-in-part of application Ser. No. 07/637,867, filed Jan. 8, 1991, now abandoned, and a 371 of International Application Ser. No. PCT/US/92/00313, filed Jan. 7, 1992, which designated the U.S.

TECHNICAL FIELD

This invention relates to biologically active vitamin $D_2$ compounds. More specifically, this invention relates to the hormonally active, natural metabolite 1α,24(S)-dihydroxy vitamin $D_2$ and to methods of preparing this metabolite and the nonbiological epimer 1α,24(R)-dihydroxy vitamin $D_2$. This invention also relates to a pharmaceutical composition which includes a pharmaceutically effective amount of 1α,24(S)-dihydroxy vitamin $D_2$, and to a method of controlling abnormal calcium metabolism by administering a pharmaceutically effective amount of the compound.

BACKGROUND OF THE INVENTION

Vitamin D and its active metabolites are known to be important in regulating calcium metabolism in animals and humans. The naturally occurring form of vitamin D in animals and humans is vitamin $D_3$. It has been shown that in animals, including humans, vitamin $D_3$ is activated by being hydroxylated in the $C_{25}$ position in the liver, followed by 1α-hydroxylation in the kidney to produce the hormone 1α,25-dihydroxy vitamin $D_3$ ["1α,25-$(OH)_2D_3$"]. See, U.S. Pat. No. 3,880,894. The major physiological pathway for catabolism of the vitamin $D_3$ metabolites, 25-hydroxy vitamin $D_3$ and 1α,25-$(OH)_2D_3$, is initiated by $C_{24}$-oxidation. Holick, M. F., Kleiner-Bossallier, A., Schnoes, H. K., Kasten, P. M., Boyle, I. T., and DeLuca, H. F., *J. Biol. Chem.*, 248, 6691–6696 (1973).

Vitamin $D_2$ is the major, naturally occurring form of vitamin D found in plants. Vitamin $D_2$ differs structurally from vitamin $D_3$ in that vitamin $D_2$ has a methyl group at $C_{24}$ and has a double bond between $C_{22}$ and $C_{23}$.

Shortly after their discovery, it seemed apparent that vitamin $D_3$ and vitamin $D_2$ had similar, if not equivalent, biological activity. It has also been commonly believed that the metabolism (i.e., the activation and catabolism) of vitamin $D_2$ was the same as for vitamin $D_3$. See, Harrison's Principles of Internal Medicine: Part Seven, "Disorders of Bone and Mineral Metabolism: Chap. 35," in E. Braunwald, K. J. Isselbacher, R. G. Petersdorf, J. D. Wilson, J. B. Martin and H. S. Fauci (eds.), *Calcium, Phosphorus and Bone Metabolism: Calcium Regulating Hormones*, McGraw-Hill, N.Y., pp. 1860–1865. In this regard, the active form of vitamin $D_2$ is believed to be 1α,25-dihydroxy vitamin $D_2$ ["1α,25-$(OH)_2D_2$"]. Further, 24-hydroxy derivatives of 25-hydroxy vitamin $D_2$ and 1α,25-$(OH)_2D_2$, that is, 24,25-dihydroxy vitamin $D_2$ and 1α,24,25-trihydroxy vitamin $D_2$, are known, suggesting that catabolism of vitamin $D_2$, like vitamin $D_3$, proceeds through the same $C_{24}$ oxidation step. Jones, G., Rosenthal, D., Segev, D., Mazur, Y., Frolow, F., Halfon, Y., Robinavich, D. and Shakked, Z., *Biochemistry*, 18:1094–1101 (1979).

It has recently been found, however, that an active analogue of vitamin $D_2$, 1α-hydroxy vitamin $D_2$ ["1α-(OH)$D_2$"] has pharmacological properties distinctly different than those exhibited by its vitamin $D_3$ counterpart, 1α-hydroxy vitamin $D_3$ ["1α-(OH)$D_3$"]. U.S. Pat. No. 5,104,864 discloses that 1α-(OH)$D_2$ will reverse the loss of bone mass in human osteoporotic patients when administered at dosages of 2.0 μg/day or higher. Because of toxicity, dosage levels of 2.0 μg/day or greater are not safely obtained with 1α-(OH)$D_3$.

Such distinct pharmacological properties may be explained fully, or in part, by the present inventors' discovery that pharmacological dosages of 1α-(OH)$D_2$ administered to humans are metabolized in part to biologically active 1α,24(S)-dihydroxy vitamin $D_2$ ["1α,24(S)-$(OH)_2D_2$"]. As explained in more detail below, the hydroxylation at the carbon-24 position of the 1-hydroxylated vitamin $D_2$ molecule, represents an activation pathway peculiar to the vitamin $D_2$ molecule.

While 1α,24(S)-dihydroxy vitamin $D_3$ and 1α,24(R)-dihydroxy vitamin $D_3$ ["1α,24(R/S)-$(OH)_2D_3$"] have been chemically synthesized (U.S. Pat. No. 4,022,891) it has not been demonstrated that either is a natural compound found in biological systems. Furthermore, the present inventors have discovered that 1α,24(S)-$(OH)_2D_2$ has distinctly different biological activity from that exhibited by 1α,24(R/S)-$(OH)_2D_3$. For example, Ishizuka et al. have found that 1α,24(R)-$(OH)_2D_3$ binds the 1,25-$(OH)_2D_3$ receptor site more tightly than does 1,25-$(OH)_2D_3$ itself. Ishizuka, S., Bannai, K., Naruchi, T. and Hashimoto, Y., *Steroids*, 37:1, 33–42 (1981); Ishizuka, S., Bannai, K., Naruchi, T. and Hashimoto, Y., *Steroids*, 39:1,53–62 (1982). Using a similar assay, the present inventors have discovered that the 1α,24 (S)-$(OH)_2D_2$ is two-fold less competitive in binding the 1,25-$(OH)_2D_3$ receptor site than is 1,25-$(OH)_2D_3$. The present inventors have also found that 1α,24(S)-$(OH)_2D_2$ shows a relatively poor binding affinity for the vitamin D serum binding protein which is evidence of a rather short half life indicative of low toxicity.

The present inventors have demonstrated the presence of circulating 1α,24(S)-$(OH)_2D_2$ in humans administered 1α-(OH)$D_2$. This indicates that in animals and man, vitamin $D_2$ is naturally metabolized to both 1α,25-$(OH)_2D_2$ and 1α,24 (S)-$(OH)_2D_2$. The relative ratios of the two vitamin $D_2$ hormones appear to vary according to the precursor and the amount of precursor presented to the $C_{24}$ pathway. Thus it appears that as dosages of 1α-(OH)$D_2$ are increased, the ratio of 1α,24(S)-$(OH)_2D_2$ to 1α,25-$(OH)_2D_2$ increases.

These results which are presented in more detail below, indicate that 1α,24(S)-$(OH)_2D_2$ has the desirable characteristic of high biological activity with low toxicity. The fact that 1α,24(S)-$(OH)_2D_2$ is a significant metabolite when pharmacological levels of 1α-(OH)$D_2$ are administered indicates that 1α,24(S)-$(OH)_2D_2$ may be mediating the desirable pharmacological effects of 1α-(OH)$D_2$ and is a useful therapeutic drug for treating various types of disorders involving calcium metabolism.

SUMMARY OF THE INVENTION

The invention provides synthetic 1α,24(S)-$(OH)_2D_2$ which is a biologically produced active form of vitamin $D_2$. The biological form may also be referred to as 1α,24(S)-dihydroxy ergocalciferol and is represented by the structure given hereinafter. The biological form of the compound has potent biological activity and rapid systemic clearance, indicating low toxicity.

The invention also encompasses a novel method of producing 1α,24(S)-dihydroxy vitamin $D_2$ which entails using ergosterol as a starting material, forming 24-hydroxy vitamin $D_2$ and then, 1α-hydroxlyating the 24-hydroxy compounds and separating the 1α,24(S)-dihydroxy vitamin D₂ epimer from the 1α,24(R)-dihydroxy vitamin D₂ epimer. In the course of this synthesis, novel intermediates are also produced.

The compound of the invention is useful in the treatment of various diseases characterized by vitamin D deficiency and various bone depletive disorders, in particular, treatment without the concomitant incidence of hypercalcemia or hypercalciuria. The compound of the invention is advantageously used as an active ingredient of pharmaceutical compositions for vitamin D deficiency diseases, for reversing or preventing the loss of bone mass or bone mineral content in persons predisposed to developing such loss, and for stabilizing bone density in persons suffering from renal osteodystrophy.

The compound of the invention is also useful as a topical agent for treatment of certain skin disorders. The compound of the invention is advantageously used as an active ingredient for topical compositions which may also include other agents capable of ameloriating skin disorders.

Other advantages and a better appreciation of the specific adaptations, compositional variations, and physical and chemical attributes of the present invention will be gained upon an examination of the following detailed description of the invention, taken in conjunction with the accompanying drawings.

BRIEF DESCRIPTION OF THE DRAWINGS

The present invention will hereinafter be described in conjunction with the appended drawings, wherein like designations refer to like elements throughout and in which:

FIG. 4 is a graph illustrating the relative binding affinities of 1α,24(S)-(OH)₂D₂ and 1α,24(R)-(OH)₂D₂.

DETAILED DESCRIPTION

The present invention provides synthetic 1α,24(S)-dihydroxy vitamin D₂ [1α,24(S)-(OH)₂-D₂].

As used herein, the terms "biological activity", "biologically active", "bioactive", or "biopotent" are meant to refer to biochemical properties of compounds such as affecting metabolism, e.g., affecting serum calcium concentration, or binding to an appropriate receptor protein, e.g., binding to vitamin D receptor protein. The term "substantially pure" in reference to compounds or substances means a purity of at least 90%.

In one of its aspects, the invention encompasses the biologically active compound of the formula (I):

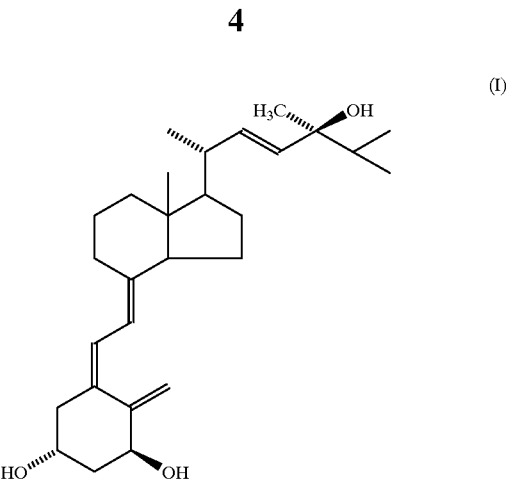

i.e., 1α,24(S)-dihydroxy Vitamin D₂.

Figure 1:
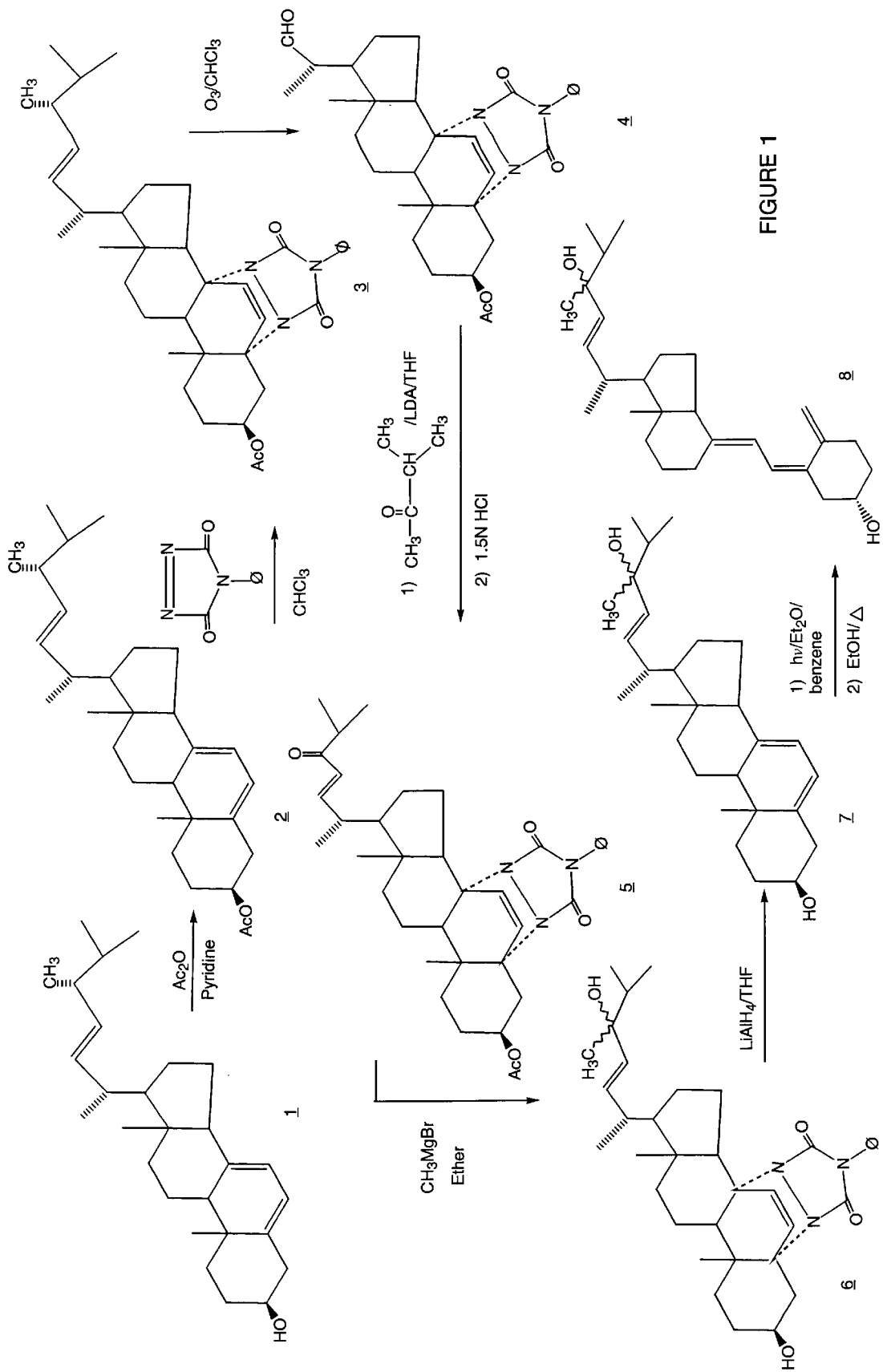
FIG. 1 illustrates preparative steps for the synthesis of 24-hydroxy vitamin D₂.
Figure 2:
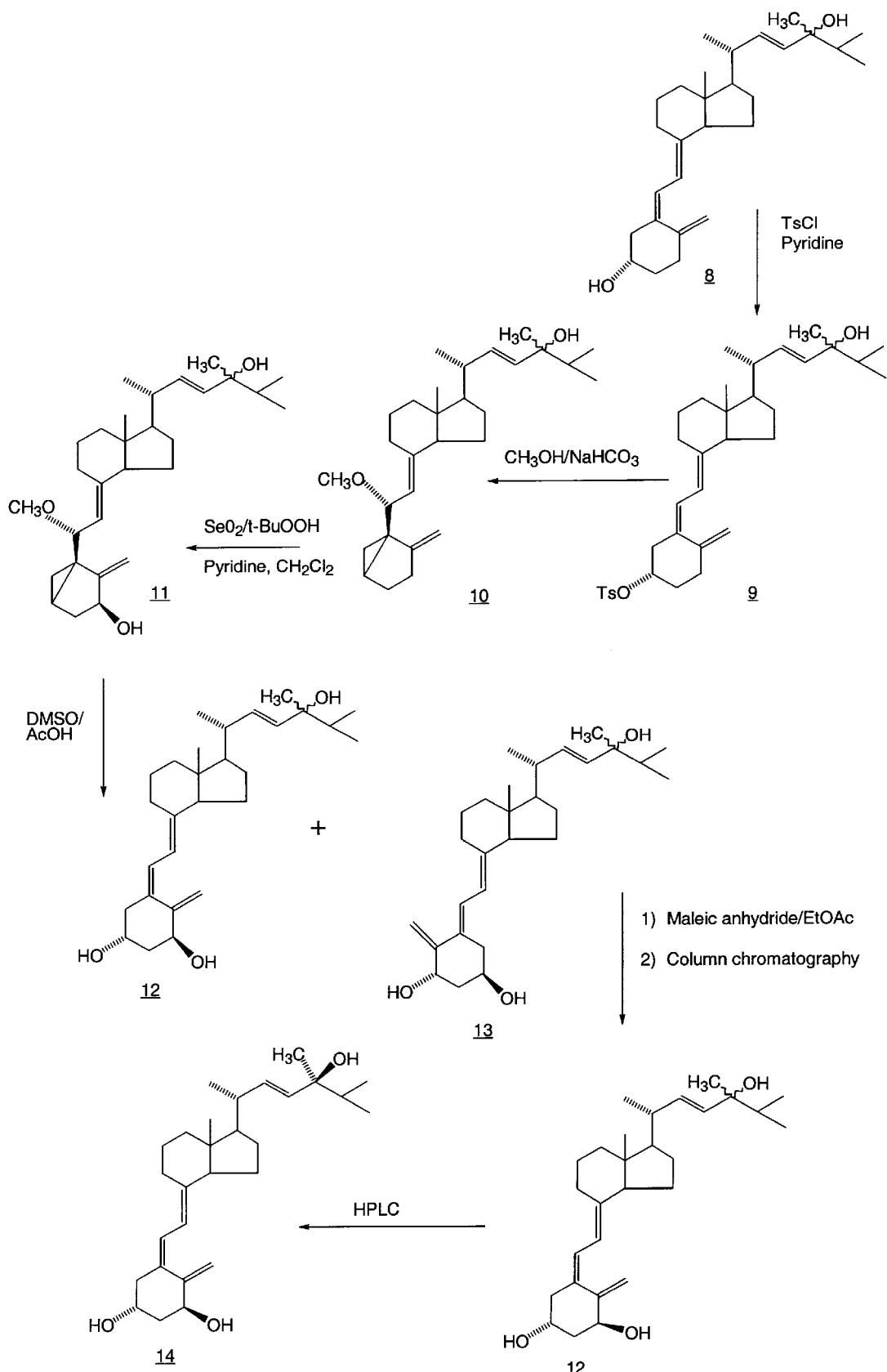
FIG. 2 illustrates preparative steps for the synthesis of 1α,24(S)-dihydroxy vitamin D₂ starting with 24-hydroxy vitamin D₂.

In another aspect, the invention involves the preparation of 1α,24(S)-dihydroxy vitamin D₂. Synthesis of 1α,24(S)-dihydroxy vitamin D₂ is accomplished according to the schema presented in FIGS. 1 and 2. Hereinafter when reference is made to a 24-hydroxy compound, unless specified, it will be presumed that the compound is an epimeric mixture of the R and S forms. As seen in FIG. 1, the synthesis uses ergosterol as the starting material. Ergosterol is converted to 24-hydroxyergosterol (5,7,22 ergostatriene-3β,24-diol (7)) by a five-step process. The 24-hydroxy ergosterol is then irradiated and thermally converted by methods well known in the art to yield 24-hydroxy vitamin D₂. As seen in FIG. 2, 24-hydroxy vitamin D₂ is then hydroxylated in a five-step process to yield 1α,24-dihydroxy vitamin D₂, using a procedure similar to that described by Paaren, et al., *J. Org. Chem.*, vol. 45, p. 3253 (1980), from which the epimers are separated.

Specifically, ergosterol is acetylated to form the 3β-acetate (2). An adduct (3) is then formed with the B-ring of the ergosterol structure by reaction of the 3β-acetate with a triazoline dione. The adduct (3) is then ozonated to truncate the side chain to form a C-21 aldehyde (4). The side chain is reestablished by reaction of the resulting aldehyde with the appropriate keto-compound to yield the 24-enone (5). The enone is then converted to the 24-methyl, 3β,24-dihydroxy adduct (6). This adduct is then reacted with a lithium aluminum hydride to deprotect the adduct and yield 24-hydroxy ergosterol (7). The 24-hydroxy ergosterol is then irradiated and thermally treated to form 24-hydroxy vitamin D₂. The 24-hydroxy vitamin D₂ is then tosylated to yield 3β-tosylate of the 24-hydroxy vitamin D₂. The tosylate is displaced by solvolysis to yield the 6-methoxy-24-hydroxy-3,5-cyclo vitamin D₂. The cyclovitamin D₂ is subjected to allylic oxidation to form the 1α, 24-dihydroxy cyclovitamin derivative. The 1α,24-dihydroxy cyclovitamin derivative is sequentially solvolyzed and subjected to a Diels-Alder type reaction which removes the 6-methoxy group and separates the 1α,24-dihydroxy vitamin D₂ (5,6 cis) from the 5,6 trans 1α,24-dihydroxy vitamin D₂.

The 1α,24-(OH)₂D₂ is subjected to reverse phase high pressure liquid chromatography to separate the two epimers and recover the epimeric form of the invention, 1α,24 (S)-(OH)₂D₂.

The compound of the invention is applicable to various clinical and veterinary fields, and is particularly useful for the treatment of abnormal metabolism of calcium and phosphorus. Specifically, 1α,24(S)-dihydroxy vitamin D₂ is intended to be used, for example, to stimulate osteoblastic activity, as measured by serum levels of osteocalcin. Osteocalcin is one of the major proteins in the bone matrix. The $1\alpha,24(S)$-dihydroxy vitamin $D_2$ binds to the vitamin D serum binding protein more weakly than does $1,25\text{-}(OH)_2 D_3$, indicative of rapid clearance and low toxicity, which enhances its pharmaceutical properties.

In a further aspect, the invention entails a method of controlling calcium metabolism, such as for treating abnormal calcium metabolism caused, e.g., by liver failure, renal failure, gastrointestinal failure, etc. The $1\alpha,24(S)$-dihydroxy vitamin $D_2$ can be used to treat prophylactically or therapeutically vitamin D deficiency diseases and related diseases, for example, renal osteodystrophy, steatorrhea, anticonvulsant osteomalacia, hypophosphatemic vitamin D-resistant rickets, osteoporosis, including postmenopausal osteoporosis, senile osteoporosis, steroid-induced osteoporosis, and other disease states characteristic of loss of bone mass, pseudodeficiency (vitamin D-dependent) rickets, nutritional and malabsorptive rickets, osteomalacia and osteopenias secondary to hypoparathyroidism, post-surgical hypoparathyroidism, idiopathic hypothyroidism, pseudoparathyroidism, and alcoholism.

$1\alpha,24(S)$-Dihydroxy vitamin $D_2$ is also of value for the treatment of hyperproliferative skin disorders such as psoriasis, eczema, lack of adequate skin firmness, dermal hydration, and sebum secretion, and is valuable for the treatment of breast and colon cancer. $1\alpha,24(S)$-Dihydroxy vitamin $D_2$ is useful as an active compound in pharmaceutical compositions having reduced side effects and low toxicity as compared with the known analogs of active forms of vitamin $D_3$, when applied, for example, to diseases induced by abnormal metabolism of calcium. These pharmaceutical compositions constitute another aspect of the invention.

The pharmacologically active compound of this invention can be processed in accordance with conventional methods of pharmacy to produce medicinal agents for administration to patients, e.g., mammals including humans. For example, the $1\alpha,24(S)$-dihydroxy vitamin $D_2$ can be employed in admixtures with conventional excipients, e.g., pharmaceutically acceptable carrier substances suitable for enteral (e.g., oral), parenteral, or topical application which do not deleteriously react with the active compound.

Suitable pharmaceutically acceptable carriers include but are not limited to water, salt solutions, alcohols, gum arabic, vegetable oils (e.g., almond oil, corn oil, cottonseed oil, peanut oil, olive oil, coconut oil), mineral oil, fish liver oils, oily esters such as Polysorbate 80, polyethylene glycols, gelatine, carbohydrates (e.g., lactose, amylose or starch), magnesium stearate, talc, silicic acid, viscous paraffin, fatty acid monoglycerides and diglycerides, pentaerythritol fatty acid esters, hydroxy methylcellulose, polyvinyl pyrrolidone, etc.

The pharmaceutical preparations can be sterilized and, if desired, be mixed with auxiliary agents, e.g., lubricants, preservatives, stabilizers, wetting agents, emulsifiers, salts for influencing osmotic pressure, buffers, coloring, flavoring and/or one or more other active compounds, for example, vitamin $D_3$ and its $1\alpha$-hydroxylated metabolites, conjugated estrogens or their equivalents, anti-estrogens, calcitonin, biphosphonates, calcium supplements, cobalamin, pertussis toxin and boron.

For parenteral application, particularly suitable are injectable, sterile solutions, preferably oily or aqueous solution, as well as suspensions, emulsions, or implants, including suppositories. Parenteral administration suitably includes subcutaneous, intramuscular, or intravenous injection, nasopharyngeal or mucosal absorption, or transdermal absorption. Ampoules are convenient unit dosages.

For enteral application, particularly suitable are tablets, dragees, liquids, drops, suppositories, lozenges, powders, or capsules. A syrup, elixir, or the like can be used if a sweetened vehicle is desired.

For topical application, suitable nonsprayable viscous, semi-solid or solid forms can be employed which include a carrier compatible with topical application and having a dynamic viscosity preferably greater than water, for example, mineral oil, almond oil, self-emulsifying beeswax, vegetable oil, white soft paraffin, and propylene glycol. Suitable formulations include, but are not limited to, creams, ointments, lotions, solutions, suspensions, emulsions, powders, liniments, salves, aerosols, transdermal patches, etc., which are, if desired, sterilized or mixed with auxiliary agents, e.g., preservatives, stabilizers, demulsifiers, wetting agents, etc. A cream preparation in accordance with the present invention suitably includes, for example, mixture of water, almond oil, mineral oil and self-emulsifying beeswax; an ointment preparation suitably includes, for example, almond oil and white soft paraffin; and a lotion preparation suitably includes, for example, dry propylene glycol.

Topical preparations of the compound in accordance with the present invention useful for the treatment of skin disorders may also include epithelialization-inducing agents such as retinoids (e.g., vitamin A), chromanols such as vitamin E, $\beta$-agonists such as isoproterenol or cyclic adenosine monophosphate (cAMP), anti-inflammatory agents such as corticosteroids (e.g., hydrocortisone or its acetate, or dexamethasone) and keratoplastic agents such as coal tar or anthralin. Effective amounts of such agents are, for example, vitamin A about 0.003 to about 0.3% by weight of the composition; vitamin E about 0.1 to about 10%; isoproterenol about 0.1 to about 2%; cAMP about 0.1 to about 1%; hydrocortisone about 0.25 to about 5%; coal tar about 0.1 to about 20%; and anthralin about 0.05 to about 2%.

For rectal administration, the compound is formed into a pharmaceutical composition containing a suppository base such as cacao oil or other triglycerides. To prolong storage life, the composition advantageously includes an antioxidant such as ascorbic acid, butylated hydroxyanisole or hydroquinone.

For treatment of calcium metabolic disorders, oral administration of the pharmaceutical compositions of the present invention is preferred. Generally, the compound of this invention is dispensed by unit dosage form comprising about 0.5 $\mu$g to about 25 $\mu$g in a pharmaceutically acceptable carrier per unit dosage. The dosage of the compound according to this invention generally is about 0.01 to about 1.0 $\mu$g/kg/day, preferably about 0.04 to about 0.3 $\mu$g/kg/day.

For topical treatment of skin disorders, the dosage of the compound of the present invention in a topical composition generally is about 0.01 $\mu$g to about 50 $\mu$g per gram of composition.

For treatment of cancers, the dosage of $1\alpha,24(S)\text{-}(OH)_2 D_2$ in a locally applied composition generally is about 0.01 $\mu$g to 100 $\mu$g per gram composition.

It will be appreciated that the actual preferred amounts of active compound in a specific case will vary according to the efficacy of the specific compound employed, the particular compositions formulated, the mode of application, and the particular site and organism being treated. For example, the specific dose for a particular patient depends on the age, body weight, general state of health and sex, on the diet, on the timing and mode of administration, on the rate of excretion, and on medicaments used in combination and the severity of the particular disorder to which the therapy is applied. Dosages for a given host can be determined using conventional considerations, e.g., by customary comparison of the differential activities of the subject compounds and of a known agent, such as by means of an appropriate conventional pharmacological protocol.

In a still further aspect, the compound of the present invention can also be advantageously used in veterinary compositions, for example, feed compositions for domestic animals to treat or prevent hypocalcemia. Generally, the compound of the present invention is dispensed in animal feed such that normal consumption of such feed provides the animal about 0.01 to about 1.0 μg/kg/day.

The following examples are to be construed as merely illustrative, and not limitative of the remainder of the disclosure in any way whatsoever. In the following examples proton nuclear magnetic resonance ($^1$H NMR) spectra were recorded with a Bruker AM-400(400 MHz) with aspect 3000 Computer in $CDCl_3$ solutions with $CHCl_3$ as an internal standard. Chemical shifts are reported in ppm. Ultraviolet spectra were recorded with a Hitachi U-2000 Spectrophotometer and are reported for ethanol solutions.

EXAMPLE 1

Generation, Purification and Identification of $1\alpha,24(?)$-$(OH)_2$ $D_2$ in Human Liver Cells Incubated with $1\alpha$-$(OH)D_2$ Substantially pure $1\alpha$-$(OH)D_2$ was obtained from Bone Care International, Inc. of Madison, Wis. The $1\alpha$-$(OH)D_2$ was cultured for 48 hours with cells derived from a human hepatoma, Hep 3B, in medium devoid of fetal calf serum using known methods in the art.

Lipid extracts of the combined medium and cells were generated by known methods in the art and were subjected to high pressure liquid chromatography (HPLC) on Zorbax-S1L developed with hexane/isopropanol/methanol (91:7:2). The putative $1\alpha,24(?)$-$(OH)_2D_2$ metabolite eluted between the parent $1\alpha$-$(OH)D_2$ and standard $1\alpha,25$-$(OH)_2D_2$ (also obtained from Bone Care International, Inc. of Madison, Wis.). (As used herein, the term "$1\alpha,24(?)$-$(OH)_2D_2$" is meant to indicate that the epimeric form has not been identified.) The $1\alpha,24(?)$-$(OH)_2D_2$ was further purified by this HPLC system before the metabolite's identification was undertaken using mass spectrometry analysis.

The purified metabolite was more polar than the starting material, $1\alpha$-$(OH)D_2$ and thus was tentatively concluded to be a dihydroxy vitamin $D_2$ metabolite. This metabolite also possessed the vitamin D chromophore, indicating retention of the cis-triene system of vitamin D. Since the metabolite was derived from $1\alpha$-$(OH)D_2$, its structure was thus $1\alpha,X$-$(OH)_2D_2$ where "X" indicates the position of the second hydroxyl group.

The trimethylsilyl-derivative of the $1\alpha,X$-$(OH)_2D_2$ was prepared according to known methods in the art and mass spectrometry was performed on the TMS-derivative and the native compound. The TMS-derivative was analyzed by GC-MS, and the identification was mainly derived from interpretation of the fragmentation pattern of the pyro-metabolite. The molecular ion possessed a m/z of 644 indicating a dihydroxy vitamin $D_2$ with addition of three TMS groups accounting for 216 units of additional mass. Since $1\alpha$-$(OH)D_2$ has 3β- and $1\alpha$-groups and the putative metabolite had one additional hydroxyl, all three hydroxyls were thus derivatized. Distinctive fragments were found at m/z 601, 511, 421, 331 representing loss of a 43 mass unit of fragment alone or in addition to one, two or three TMS groups of 90 units each. This pattern was most likely explained by cleavage of the C-24 to C-25 bond loss of $C_3H_7$ accounting for 43 mass units. This represents loss of the $C_{26}$-$C_{25}$-$C_{27}$ fragment. Furthermore, the mass spectrum lacked the m/z 131 fragment characteristic of all 25-hydroxylated vitamin D compounds.

The mass spectrum showed the m/z 513 fragment indicating loss of 131 mass units due to A-ring cleavage with loss of $C_2$-$C_3$-$C_4$ also characteristic of vitamin D compounds. The mass spectrum also contained m/z 143 which was probably derived from C-24 to C-23 cleavage and a loss of a methyl group. The unusual loss of 43 units indicating $C_{24}$-$C_{25}$ fragility coupled with the loss of a fragment due to $C_{23}$-$C_{24}$ cleavage indicated that the extra hydroxyl in $1\alpha,X$-$(OH)_2D_2$ was at carbon-24. Thus, the structure was identified as $1\alpha,24(?)$-$(OH)_2D_2$.

The native metabolite was analyzed by direct probe mass spectrometry. This analysis was consistent with a hydroxyl in the 24 position, and was also consistent with the GC-MS analysis of the TMS-derivative described above. The native metabolite showed the expected molecular ion at m/z 428 and a distinctive fragment at m/z 367, indicating the loss of one water and the $C_{25}$-$C_{26}$-$C_{27}$ fragment of 43 mass units.

EXAMPLE 2

Synthesis of $1\alpha,24(S)$-dihydroxy Vitamin $D_2$ (22E)-5,7,22-ergostatriene-3β-yl Acetate (2)

To a solution of 50 gm (0.13 mol) of ergosterol (1) in 300 ml of anhydrous pyridine was added 33.3 ml (0.35 mol) of acetic anhydride. The mixture was stirred at room temperature overnight and then 600 ml of water was added. The precipitate was filtered and washed three times with 200 ml portions of acetonitrile and then air dried to yield 42.0 g (74%) of (2).

22-oxo-5α,8α-(4-phenyl-3,5-dioxo-1,2,4-triazolidine-1,2-diyl)23,24-dinor-6-cholene-3β-yl Acetate (4)

To a solution of 33.0 g (0.075 mol) of ergosterol acetate (2) in 1000 ml of chloroform was added 13.2 g (0.075 mol) of 4-phenyl-1,2,4-triazoline-3,5-dione. The solution of the thus formed (3) was stirred at room temperature for 30 min. and then 5 ml of pyridine was added. The solution was cooled to −78° C. and treated at −78° C. with an ozone-oxygen mixture for 2 hours and then thoroughly purged with nitrogen. Then 50 ml of dimethylsulfoxide was added and the mixture was washed with 300 ml of water, then twice with 200 ml of 2N HCl and finally 300 ml of water. The organic layer was separated, dried over anhydrous $MgSO_4$ and concentrated to dryness in vacuo. The residue was purified on a silica gel column using 30% ethyl acetate in hexane to yield 16.0 g (39%) of the title compound as a foamy solid.

$^1$H NMR: (400 MHz; $CDCl_3$): δppm 0.85 (3H, s, 18-$CH_3$), 1.10 (3H, s, 19-$CH_3$), 1.15 (3H, d, 21-$CH_3$), 1.99 (3H, s, 3β-$CH_3CO$), 5.45 (1H, m, 3α-H), 6.26 (1H, d. 7-H), 6.40 (1H, d, 6-H), 7.42 (5H, m, Ph), 9.58 (1H, d, HCO).

(22E)5α,8α-(4-phenyl-3,5-dioxo-1,2,4-triazolidine-1,2-diyl) Cholesta-6,22-diene-24-one-3β-yl Acetate (5)

Butyllithium (1.6M solution in hexane 8.94 ml, 0.014 mol) was added to a stirred, cooled (0° C.) solution of diisopropylamine (1.45 g, 0.014 mol) in dry tetrahydrofuran (20 ml) under nitrogen. 3-Methylbutan-2-one (1.23 g, 0.014 mol) in dry tetrahydrofuran (6 ml) was added dropwise at 0° C. over 15 min. The solution was stirred at 0° C. for 1 hr. more, then cooled to −70° C. and a solution of the aldehyde (4) (6.0 g, 0.011 mol) in dry tetrahydrofuran (60 ml) was added. The temperature was raised to −20° C. and kept at this temperature for 3 hrs. Then glacial acetic acid (20 ml) was added at −20° C. and the solution was brought to room temperature. Ether (800 ml) and water (400 ml) were added and the organic layer was separated and washed with 10% hydrochloric acid (2×300 ml), saturated sodium bicarbonate solution (2×300 ml), and water (2×300 ml). Concentration gave the crude product (7.5 g) which was dissolved in tetrahydrofuran (100 ml) containing 1.5 N-hydrochloric acid (12 ml). After refluxing for 1.5 hrs., the mixture was diluted with ether (600 ml), washed with a 5% sodium carbonate solution (2×200 ml) and water (2×200 ml), and dried (anhydrous $MgSO_4$). Concentration under reduced pressure gave the crude product (7.0 g). Chromatography over silica gel (50% ethyl acetate in hexane) gave the enone (5) 4.0 g (59%).

$^1$H NMR: (400 MHz): δppm 0.83 (3H, s. 18-$CH_3$), 0.99 (3H, s, 19-$CH_3$), 1.09 (6H, dd, 26 and 27-$CH_3$), 1.12 (3H, d, 21-$CH_3$), 2.0 (3H, s, 3β-$CH_3CO$), 2.84 (1H, m, 25-H), 5.45 (1H, m, 3α-H), 6.06 (1H, d, 23-H), 6.24 (1H, d, 7-H), 6.39 (1H, d, 6-H), 6.71 (1H, dd, 22-H), 7.42 (5H, m, Ph).

(22E)-5α,8α-(4-phenyl-3,5-dioxo-1,2,4-triazolidine-1,2-diyl)-6,22-ergostadiene-3β,24-diol (6)

The enone (5) (3.5 g, 5.7 mmol) in dry ether (100 ml) was cooled to 0° C. and methylmagnesium bromide (3.0 M solution in ether 6.8 ml, 0.02 mol) was added dropwise. After 1 hr. at 0° C., saturated ammonium chloride (100 ml) was added. The organic layer was separated. The aqueous layer was extracted with ether (2×200 ml). The combined ether phases were dried over anhydrous $MgSO_4$ and concentrated to dryness in vacuo to yield the crude product 3.0 g (90%) of (6).

(22E)-5,7,22-ergostatriene-3β,24-diol (7)

To a solution of 3.0 g (5.1 mmol) of (6) in dry tetrahydrofuran (250 ml) was added 3.6 g (0.09 mol) of lithium aluminum hydride. The mixture was heated under reflux for 3 hrs., cooled with ice water bath and reaction mixture decomposed by the cautious dropwise addition of ice water (5 ml). The mixture was filtered and the filtrate was concentrated in vacuo to remove most of the tetrahydrofuran. The residue was dissolved in 200 ml of ethyl acetate and washed twice with saturated NaCl solution (2×200 ml), dried over anhydrous $MgSO_4$ and concentrated in vacuo. The residue was purified on a silica gel column using 30% ethyl acetate in hexane to yield 1.5 g (71%) of (7).

$^1$H NMR: (400 MHz, $CDCl_3$): δppm 0.64 (3H, s, 18-H), 0.88 (6H, dd, 26 and 27-$CH_3$), 0.93 (3H, s, 19-$CH_3$), 1.06 (3H, d, 21-$CH_3$), 1.19 (3H, s, 28-$CH_3$), 3.55 (1H, m, 3α-H), 5.36 (1H, d, 7-H), 5.42 (2H, m, 22 and 23-H), 5.52 (1H, d, 6-H). UV (ethanol) $\lambda_{max}$: 282 nm.

24-hydroxyvitamin $D_2$ (8)

One gram (2.4 mmol) of (7) was dissolved in 250 ml of ether and benzene (4:1) and irradiated with stirring under nitrogen in a water-cooled quartz immersion well using a Hanovia medium-pressure UV lamp for 2 hrs. The solution was concentrated in vacuo, redissolved in 100 ml of ethanol and heated under reflux overnight. The solution was concentrated to dryness in vacuo and the residue was purified on a silica gel column using 30% ethyl acetate in hexane to yield 0.55 g (55%) of (8).

$^1$H NMR: (400 MHz, $CDCl_3$): βppm 0.57 (3H, s, 18-$CH_3$), 0.92 (6H, dd, 26 and 27-$CH_3$), 1.06 (3H, d, 21-$CH_3$), 1.20 (3H, s, 28-$CH_3$), 3.93 (1H, m, 3-H), 4.79 (1H, m (sharp), 19-H), 5.01 (1H, m, (sharp), 19-H), 5.43 (2H, m, 22 and 23-H), 6.02 (1H, d, 7-H), 6.22 (1H, d, 6-H). UV (ethanol) $\lambda_{max}$: 265 nm.

24-hydroxyvitamin $D_2$ Tosylate (9)

To a solution of 0.55 g (1.3 mmol) of (8) dissolved in 5 ml of anhydrous pyridine was added 0.6 g (3.2 mmol) of tosyl chloride. The mixture was stirred under nitrogen at 5° C. for 20 hrs. The reaction mixture was poured into 100 ml of cold saturated $NaHCO_3$ solution and extracted with ether (3×100 ml). The combined organic extracts were washed with 5% HCl solution (2×200 ml) saturated sodium bicarbonate solution (2×200 ml) and saturated NaCl solution (2×200 ml), dried over anhydrous $MgSO_4$ and concentrated in vacuo to yield 0.62 g (84%) of (9).

$^1$H NMR: (400 MHz, $CDCl_3$): δppm 0.57 (3H, s, 18-$CH_3$), 0.92 (6H, dd, 26 and 27-$CH_3$), 1.08 (3H, d, 21-$CH_3$), 1.24 (3H, s, 28-$CH_3$), 2.43 (3H, s, $CH_3$ (tosylate)), 4.69 (1H, m, 3-H), 4.77 (1H, m, (sharp), 19-H), 5.0 (1H, m, (sharp), 19-H), 5.42 (2H, m, 22 and 23-H), 6.03 (1-H, d, 7-H), 6.25 (1-H, d, 6-H) 7.31 and 7.83 (4H, d, aromatic).

24-hydroxy-3,5-cyclovitamin $D_2$ (10)

To a solution of 0.6 g (1.06 mmol) of (9) dissolved in 50 ml of anhydrous methanol was added sodium bicarbonate 4.0 (0.047 mol). The mixture was heated at reflux for 6 hrs. The reaction mixture was concentrated in vacuo. Water (100 ml) was added followed by extraction with ether (2×200 ml). The combined ether extracts were dried over anhydrous $MgSO_4$ and concentrated to dryness in vacuo to yield 450 mg (100%) of (10) as an oil.

1α,24-dihydroxy-3,5-cyclovitamin $D_2$ (11) tert-Butyl hydroperoxide (870 μl (2.61 mmol); 3M in toluene) was added to a suspension of 73 mg (0.66 mmol) of selenium dioxide in 50 ml of anhydrous dichloromethane under nitrogen. The mixture was stirred at room temperature under nitrogen for 3 hrs. Then 0.1 ml of anhydrous pyridine was added followed by a solution of 450 mg (1.06 mmol) of (10) dissolved in 15 ml of anhydrous dichloromethane. The mixture was stirred under nitrogen at room temperature for 10 min. then 25 ml of 10% NaOH solution was added and the mixture was extracted with ether (3×100 ml). The combined ether extracts were washed with 10% NaOH solution (2×100 ml), water (2×100 ml), saturated sodium chloride solution (2×100 ml), dried over anhydrous $MgSO_4$ and concentrated to dryness in vacuo. The residue was purified on a silica gel column using a mixture of 30% ethyl acetate in hexane to yield 110 mg (24%) of (11).

$^1$H NMR: (400 MHz, $CDCl_3$): δppm, 0.55 (3H, s, 18$CH_3$), 0.90 (6H, dd, 26 and 27-$CH_3$), 1.03 (3H, d, 21-$CH_3$), 1.19 (3H, s, 28-$CH_3$), 3.25 (3H, s, —$OCH_3$), 4.19 (1H, d, 6-H), 4.19 (1H, m, 1-H), 4.92 (2H, d, 7-H), 5.15 (1H, m, (sharp), 19-H), 5.2 (1H, m, (sharp), 19-H), 5.42 (2H, m, 22 and 23-H).

5,6-cis and 5,6-trans-1α,24-dihydroxy Vitamin $D_2$ (12, 13)

1α,24-dihydroxy-3,5-cyclovitamin $D_2$ (11) 110 mg (0.25 mmol) was dissolved in 2.0 ml of dimethylsulfoxide and 1.5 ml of acetic acid and heated at 50° C. under nitrogen for 1 hr. The solution was poured over ice and 50 ml of saturated $NaHCO_3$ solution. The mixture was extracted with ether (3×100 ml). The combined ether extracts were washed with saturated $NaHCO_3$ solution (3×100 ml), water (2×100 ml), saturated NaCl solution (2×200 ml), dried over anhydrous $MgSO_4$ and concentrated in vacuo to yield the crude product 100 mg (93%) of (12) and (13).

5,6-cis-1α,24-dihydroxy Vitamin $D_2$ (12)

To a solution of (12) and (13) in 5 ml of ethyl acetate was added 20 mg (0.2 mmol) of maleic anhydride and the mixture was stirred at 35° C. for 24 hrs. under nitrogen. The solution was concentrated to dryness in vacuo. The residue was purified on a silica gel column using 50% ethyl acetate in hexane to yield 20 mg (22%) of (12).

$^1$H NMR: (400 MHz, $CDCl_3$): δppm 0.57 (3H, s, 18-$CH_3$), 0.89 (6H, dd, 26 and 27-$CH_3$), 1.04 (3H, d, 21-$CH_3$), 1.21 (3H, s, 28-$CH_3$), 4.23 (1H, m, 3-H), 4.40 (1H, m, 1-H), 5.0 (1H, m, (sharp), 19-H), 5.33 (1H, m, (sharp), 19-H), 5.44 (2H, m, 22 and 23-H), 6.01 (1H, d, 7-H), 6.37 (1H, d, 6-H). UV (ethanol) $\lambda_{max}$: 265 nm.

1α,24(S)-dihydroxy Vitamin $D_2$ (14)

The 24 epimers of 1α,24-$(OH)_2D_2$ were separated by high pressure liquid chromatography, performed on a Waters instrument using a reverse-phase Supelco C-8 prep. column (25 cm×21.2 mm; particle size 12 μm) with the solvent system, acetonitrile:water, 60:40, 10 mL/min. The epimers were given the designations epimer 1 and epimer 2. Under these conditions the retention time of epimer 1 was 63 min., and the retention time of epimer 2 was 71 min. Using x-ray crystallography, it was determined that the stereochemistry of epimer 2 was 1α,24(R)-$(OH)_2D_2$. The stereochemistry of epimer 1 was therefore known to be 1α,24 (S)-$(OH)_2D_2$

EXAMPLE 3

Identification of the Stereochemistry and the Biologically Derived 1α,24(?)-$(OH)_2D_2$ Metabolite by Comparison to the Chemically Synthesized Epimers, 1α,24(S)-$(OH)_2D_2$ and 1α,24(R)-$(OH)_2D_2$.

Figure 3:
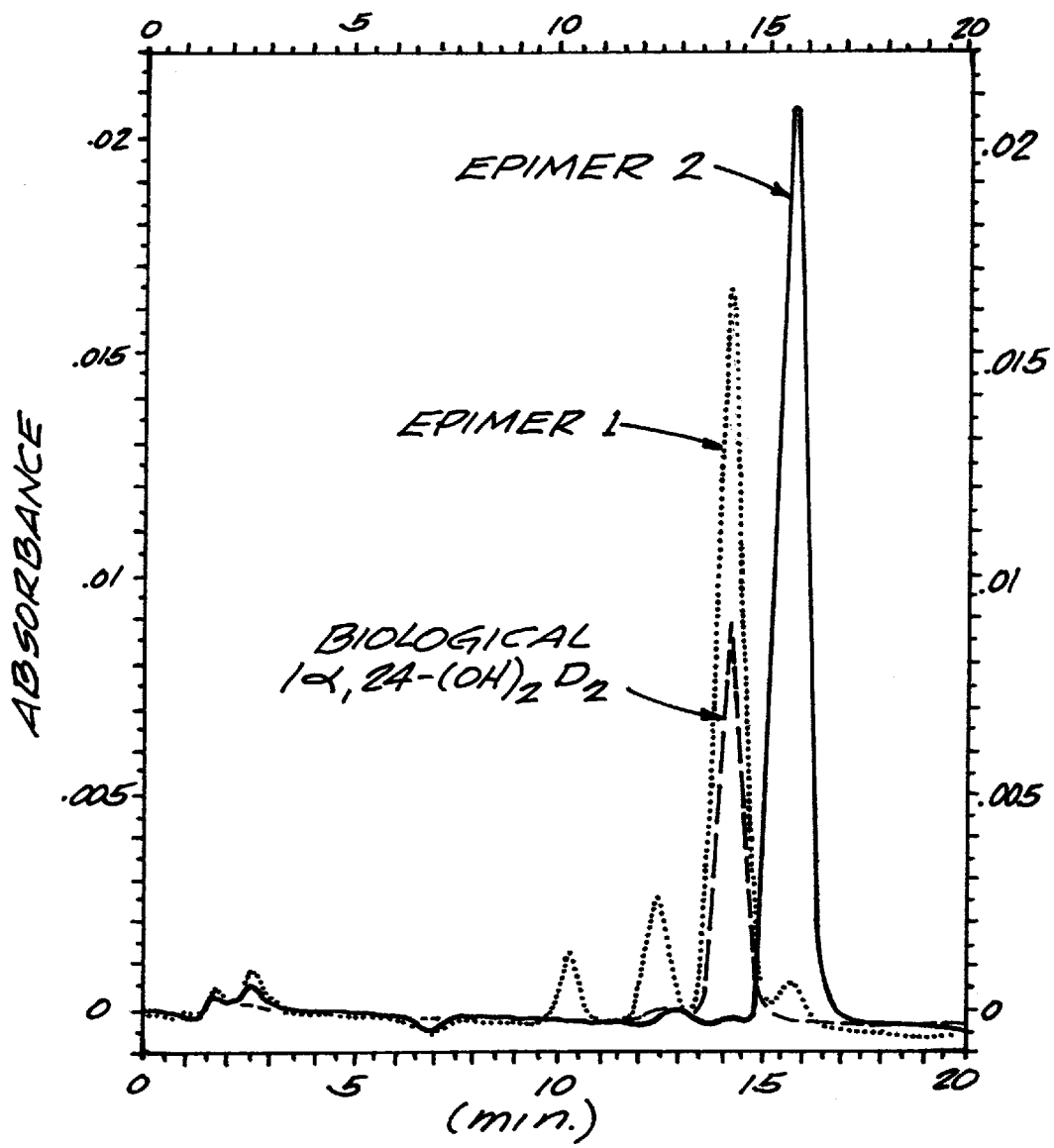
FIG. 3 is a reverse phase high pressure liquid chromatography profile of biological 1α,24-dihydroxy vitamin D₂ and the R and S epimers of synthetic 1α,24-dihydroxy vitamin D₂.

The stereochemistry of the biologically generated metabolite obtained as described in example 1, above, was compared by high pressure liquid chromatography and gas chromatography to the chemically synthesized epimers obtained as described in example 2, above. Based on these comparisons, it was determined that the biologically produced metabolite has the structure, 1α,24(S)-$(OH)_2D_2$. FIG. 3 shows a profile of the high pressure liquid chromatography experiment making this comparison. In FIG. 3, epimer 1 is the chemically synthesized 1α,24(S)-$(OH)_2D_2$.

(a) High pressure liquid chromatographic comparisons utilized two different columns and solvent systems. On the reverse-phase column Zorbax-ODS (Dupont Instruments; 3μ; 6.2 mm×8 cm) utilizing the solvent system, acetonitrile:water, 60:40, 1 ml/min., the biological metabolite emerged at 14.3 min. and 1α,24(S)-$(OH)_2D_2$ ran at 14.2 min.; however, 1α,24(R)-$(OH)_2D_2$ ran at 15.7 min.

On the straight-phase column Zorbax-SIL (Dupont Instruments; 3μ; 6.2 mm×8 cm) utilizing the solvent system, hexane:isopropanol:methanol, 94:5:1, 1 ml/min., the biological metabolite emerged at 22.4 min. and 1α,24(S)-$(OH)_2D_2$ ran at 22.4 min.; however, 1α,24(R)-$(OH)_2D_2$ ran at 22.8.

(b) With gas chromatography, 1α,24(S)-$(OH)_2D_2$ co-migrated with the biologically generated compound whereas the retention time of 1α,24(R)-$(OH)_2D_2$ was quite different (Table 1).

TABLE 1

Gas Chromatography Retention Times of Pyro-Derivatives Relative to Pyro-1α,25-$(OH)_2D_3$.

| Compound | Relative Retention Time* |
|---|---|
| 1α,24(S)-$(OH)_2D_2$ | 1.0165 |
| 1α,24(R)-$(OH)_2D_2$ | 1.0098 |
| Biological Metabolite | 1.0163 |

*Retention time is expressed relative to an internal standard 1α,25-$(OH)_2D_3$ where the pyro-derivatives are compared.

EXAMPLE 4

Comparison of the Biological Activity of 1α,24(S)-$(OH)_2D_2$ and 1α,24(R)-$(OH)_2D_2$.

The biological activity in vitro of chemically synthesized 1α,24(S)-$(OH)_2D_2$ and 1α,24(R)-$(OH)_2D_2$ was measured using a vitamin D-dependent transcriptional activation model system in which a vitamin D receptor (VDR)-expressing plasmid pSG5-hVDR1/3 and a plasmid p(CT4)[4]TKGH containing a Growth Hormone (GH)-gene, under the control of a vitamin D-responsive element (VDRE) were co-transfected into Green monkey kidney, COS-1 cells. DNA's for these two vectors were supplied by Dr. Mark Haussler, Department of Biochemistry, University of Arizona, Tucson, Ariz.

Tranfected cells were incubated with vitamin D metabolites and growth hormone production was measured. As shown in Table 2, 1α,24(S)-$(OH)_2D_2$ has significantly more activity in this system than 1α,24(R)-$(OH)_2D_2$.

TABLE 2

Vitamin D Inducible Growth Hormone Product in Transfected COS-1 Cells.

| | | Vitamin D-Inducible Growth Hormone Production | |
|---|---|---|---|
| Inducer | Molar Concentration | Total GH Production* (ng/ml) | Net vitamin D-inducible GH-production (ng/ml) |
| Ethanol | | 44 | 0 |
| 25-OH-$D_3$ | $10^{-7}$ | 245 | 201 |
| | $10^{-6}$ | 1100 | 1056 |
| | $10^{-5}$ | 775 | 731 |
| 1α,25-$(OH)_2D_3$ | $10^{-10}$ | 74 | 30 |
| | $10^{-9}$ | 925 | 881 |
| | $10^{-8}$ | 1475 | 1441 |
| 1α,25(S)-$(OH)_2D_2$ | $5 \times 10^{-10}$ | 425 | 381 |
| | $5 \times 10^{-9}$ | 1350 | 1306 |
| | $5 \times 10^{-8}$ | 1182 | 1138 |
| 1α,25(R)-$(OH)_2D_2$ | $10^{-9}$ | 80 | 36 |
| | $10^{-8}$ | 1100 | 1056 |
| | $10^{-7}$ | 1300 | 1256 |

*Averages of duplicate determinations

EXAMPLE 5

Affinity of 1α,24(S)-$(OH)_2D_2$ for the Vitamin D Receptor.

The affinity of 1α,24(S)-$(OH)_2D_2$ for the mammalian vitamin D receptor (VDR) was assessed using a commercially available kit of bovine thymus VDR and standard 1,25-$(OH)_2$-$D_3$ solutions from Incstar (Stillwater, Minn.). Purified 1α,24(S)-$(OH)_2D_2$ was quantitated by photodiode array spectrophotometry and assayed in the radioreceptor assay. The half-maximal binding of 1α,24(S)-$(OH)_2D_2$ was approximately 150 μg/ml whereas that of 1α,25-$(OH)_2D_2$ was 80 pg/ml. Thus, the 1α,24(S)-$(OH)_2D_2$ had a two-fold lower affinity for bovine thymus VDR than does 1α,25-$(OH)_2D_3$, indicating that 1α,24(S)-$(OH)_2D_2$ had potent biological activity.

EXAMPLE 6

Relative Affinities of 1α,24(S)-$(OH)_2D_2$ and 1α,24(R)-$(OH)_2D_2$ for the Vitamin D Receptor.

The relative affinities of 1α,24(R)-$(OH)_2D_2$ and 1α,24(S)-$(OH)_2D_2$ for the vitamin D receptor (VDR) were assessed using commercially available reagents of bovine thymus VDR and standard 1α,25-$(OH)_2D_3$ solutions from Incstar (Stillwater, Minn.). The purified 1α,24(R)-$(OH)_2D_2$ and 1α,24(S)-$(OH)_2D_2$ epimers were quantitated by ultraviolet spectroscopy. The concentration of 1α,24(R)-$(OH)_2D_2$ required to produce the same displacement of $^3$H-1α,25-$(OH)_2D_3$ tracer from the receptor was 20 to 30 times that required for 1α,24(S)-$(OH)_2D_2$, as shown in FIG. 4. These data indicate that the activity of the 1α,24(S)-$(OH)_2D_2$ epimer is significantly greater than that of the 1α,24(R)-$(OH)_2D_2$ epimer.

EXAMPLE 7
Affinity of 1α,24(S)-(OH)$_2$D$_2$ for the Vitamin D Serum Binding Protein.

The affinity of 1α,24(S)-(OH)$_2$D$_2$ for the vitamin D serum binding protein (DBP) was assessed using vitamin D deficient rat serum according to known methods in the art. The data indicated that the 1α,24(S)-(OH)$_2$D$_2$ binding of DBP was at least 1000 times weaker than that for 25-OH-D$_3$. Given the strong binding of 1α,24(S)-(OH)$_2$D$_2$ for the VDR and weak binding for the DBP, this compound would tend to be taken up by target cells, thus possessing a potent biological activity. In addition, the weak binding by the DBP was indicative of more rapid clearance, allowing for low toxicity.

Thus, the preceding assays demonstrated that the new 1α,24(S)-(OH)$_2$D$_2$ exhibited a distinct and unique spectrum of activities—namely, high biological potency and low toxicity which clearly distinguished the compound from those of the prior art and from its 24(R) epimer.

EXAMPLE 8
Generation of 1α,24(S)-(OH)$_2$D$_2$ from Vitamin D$_2$ and 24-OH-D$_2$.

Vitamin D$_2$ or 24-OH-D$_2$ was administered (either oral or intraperitoneal supplementation) to vitamin D-deficient rats. Lipid extracts of the plasma were prepared and the metabolites purified by the method of Horst et al. (Horst, R. L., Koszewski, N. J. and Reinhardt, T. A., Biochem., 29:578–82 (1990)) described below for synthesyzing standard biological 1α,24-(OH)$_2$D$_2$.

Standard biological 1α,24-(OH)$_2$D$_2$ was synthesized in vitro from 24-OH-D$_2$ by incubating 10 μg of 24-OH-D$_2$ in flask containing 5 ml of 20% kidney homogenates made from vitamin D-deficient chicks. The product of this reaction was isolated by HPLC and identified by mass spectrometry. In the lipid extracts of the plasma from the vitamin D-deficient rats administered vitamin D$_2$ or 24-OH-D$_2$, one metabolite isolated co-migrated on HPLC with the standard 1α,24-(OH)$_2$D$_2$, indicating that 1α,24-(OH)$_2$D$_2$ is a natural metabolite of vitamin D$_2$. In contrast, comparable rats administered vitamin D$_3$ had no detectable 24-OH-D$_3$.

EXAMPLE 9
Preferential Production of 1α,24(S)-(OH)$_2$D$_2$ with Increased Substrate Concentrations in Vitro.

Hep 3B cells were incubated with 1α-OH-D$_2$, as described above, at final concentrations of 1, 10, or 100 nM (Experiment 1), and 1 or 10 μM (Experiment 2) and 1α,24 (S)-(OH)$_2$D$_2$ was extracted and purified. The 1α,24(S)-(OH)$_2$D$_2$ and 1α,25-(OH)$_2$D$_2$ metabolites were quantitated by recovered radiolabel (Experiment 1) or by photodiode array spectrophotometry (Experiment 2). As shown in Table 3, the amount of 1α,24(S)-(OH)$_2$D$_2$ increased relative to the amount of 1α,25-(OH)$_2$D$_2$ as the substrate concentration was raised. This indicates that in this system 1α,24(S)-(OH)$_2$D$_2$ was the predominant natural active metabolite of 1α-OH-D$_2$ at higher substrate concentrations.

TABLE 3

| EXPERIMENT | SUBSTRATE CONCENTRATION | PRODUCT FORMED |
|---|---|---|
| | | Ratio of 1α,24(S)-(OH)$_2$D$_2$ to 1α,25-(OH)$_2$D$_2$ |
| 1 | nM | |
| | 1 | 1:4 |
| | 10 | 1:1 |
| | 100 | 1.5:1 |

TABLE 3-continued

| EXPERIMENT | SUBSTRATE CONCENTRATION | PRODUCT FORMED | |
|---|---|---|---|
| | | Rate of Production, pmol per 10$^6$ cells/day | |
| | | 1α,24(S)-(OH)$_2$D$_2$ | 1α,25-(OH)$_2$D$_2$ |
| 2 | μM | | |
| | 1 | 4.9 | N.D.* |
| | 10 | 59 | 7.4 |

*N.D. means not detectable

EXAMPLE 10
Production of 1α,24(S)-(OH)$_2$D$_2$ in Osteoporotic Women Administered 1α-(OH)$_2$D$_2$.

An increase in the production of 1α,24(S)-(OH)$_2$D$_2$ relative to 1α,25-(OH)$_2$D$_2$ has also been observed by the present inventors in human females who received 1α-OH-D$_2$ as part of an investigation of that drug for the treatment of osteoporosis. Following either a single dose of 2 μg of 1α-OH-D$_2$ or daily doses of 8 μg/day for one week, blood was collected and analyzed for the metabolites 1α,24(S)-(OH)$_2$D$_2$ and 1α,25-(OH)$_2$D$_2$. Lipid was extracted from the blood, and the metabolites were purified by HPLC using standard methods and quantified with the radioreceptor assay produced by Incstar (Stillwater, Minn.). One day after a single 2 μg dose, the level of 1α,24(S)-(OH)$_2$D$_2$ was undetectable with the 1α,25-(OH)$_2$D$_2$ level being approximately 11 pg/ml. In contrast, one day following the last dose of 8 μg, the level of 1α,24(S)-(OH)$_2$D$_2$ averaged 9 pg/ml with the 1α,25-(OH)$_2$D$_2$ level averaging 30 pg/ml.

EXAMPLE 11
Dose Ranging Study in Postmenopausal Osteoporotic Women.

Twenty postmenopausal osteoporotic women are enrolled in an open label study. The selected patients have ages between 55 and 75 years, and exhibit L2-L3 vertebral bone mineral density between 0.7 and 1.05 g/cm$^2$, as determined by measurements with a LUNAR Bone Densitometer (Lunar Corporation, Madison, Wis.).

On admission to the study, all patients receive instruction on selecting a daily diet containing 400 to 600 mg of calcium. Compliance to this diet is verified at weekly intervals by 24-hour food records and by interviews with each patient.

All patients complete a one-week baseline period, a five-week treatment period, and a one-week post-treatment observation period. During the treatment period, patients orally self-administer 1α,24(S)-dihydroxy vitamin D$_2$ at an initial dose of 0.5 μg/day for the first week, and at successively higher doses of 1.0, 2.0, 4.0, and 8.0 μg/day in each of the following four weeks. All doses are administered before breakfast.

Blood and urine chemistries are monitored on a weekly basis throughout the study. Key blood chemistries include fasting serum levels of calcium, phosphorus, osteocalcin, creatinine, and blood urea nitrogen. Key urine chemistries include 24-hour excretion of calcium, phosphorus, and creatinine.

Blood and urine data from this clinical study indicate that this compound does not adversely affect kidney function, as determined by creatinine clearance and blood levels of urea nitrogen; nor does it increase urinary excretion of hydroxyproline, indicating the absence of any stimulatory effect on bone resorption. The compound has no effect on any routinely monitored serum parameters, indicating the absence of adverse metabolic effects.

A positive effect of 1α,24(S)-dihydroxy vitamin $D_2$ on calcium homeostasis is evident from modest increases in 24-hour urinary calcium levels, confirming that the compound increases intestinal calcium absorption, and from increases in serum osteocalcin levels, indicating that the compound stimulates the osteoblasts.

EXAMPLE 12
Preventive Treatment of Bone Mass Loss in Postmenopausal Osteoporotic Women.

A clinical study is conducted with postmenopausal osteoporotic out-patients having ages between 55 and 75 years. The study involves up to 120 patients randomly divided into three treatment groups and continues for 24 to 36 months. Two of the treatment groups receive constant dosages of 1α,24(S)-dihydroxy vitamin $D_2$ (u.i.d.; two different dose levels at or above 1.0 μg/day) and the other group receives a matching placebo. All patients maintain a normal intake of dietary calcium (500 to 800 mg/day) and refrain from using calcium supplements. Efficacy is evaluated by pre-and post-treatment comparisons of the patient groups with regard to (a) total body calcium retention, and (b) radial and spinal bone mineral density as determined by dual-photon absorptiometry (DPA) or dual-energy x-ray absorptiometry (DEXA). Safety is evaluated by comparisons of urinary hydroxyproline excretion, serum and urine calcium levels, creatinine. clearance, blood urea nitrogen, and other routine determinations.

The results show that patients treated with 1α,24(S)-dihydroxy vitamin $D_2$ exhibit significantly higher total body calcium, and radial and spinal bone densities relative to patients treated with placebo. The monitored safety parameters confirm an insignificant incidence of hypercalcemia or hypercalciuria, or any other metabolic disturbance with 1α,24(S)-dihydroxy vitamin $D_2$ therapy.

EXAMPLE 13
Prophylaxis of Postmenopausal Bone Loss.

A clinical study is conducted with healthy postmenopausal women having ages between 55 and 60 years. The study involves up to 80 patients randomly divided into two treatment groups, and continues for 24 to 36 months. One treatment group receives a constant dosage of 1α,24(S)-dihydroxy vitamin $D_2$ (u.i.d.; a dose level at or above 1.0 μg/day) and the other receives a matching placebo. The study is conducted as indicated in Example 2 above.

The results show that patients treated with 1α,24(S)-dihydroxy vitamin $D_2$ exhibit reduced losses in total body calcium, radial or spinal bone densities relative to baseline values. In contrast, patients treated with placebo show significant losses in these parameters relative to baseline values. The monitored safety parameters confirm the safety of long-term 1α,24(S)-dihydroxy vitamin $D_2$ administration at this dose level.

EXAMPLE 14
Management of Hypocalcemia and the Resultant Metabolic Bone Disease in Chronic Hemodialysis Patients.

A twelve-month, double-blind, placebo-controlled clinical trial is conducted with thirty men and women with renal disease who are undergoing chronic hemodialysis. All patients enter an 8-week control period during which time they receive a maintenance dose of Vitamin $D_3$ (400 IU/day). After this control period, the patients are randomized into two treatment groups: one group receives a constant dosage of 1α,24(S)-dihydroxy vitamin $D_2$ (u.i.d.; a dosage greater than 3.0 μg/day) and the other group receives a matching placebo. Both treatment groups receive a maintenance dosage of Vitamin $D_3$, maintain a normal intake of dietary calcium, and refrain from using calcium supplements. Efficacy is evaluated by pre- and post-treatment comparisons of the two patient groups with regard to (a) direct measurements of intestinal calcium absorption, (b) total body calcium retention, (c) radial and spinal bone mineral density, or (d) determinations of serum calcium. Safety is evaluated by regular monitoring of serum calcium.

Analysis of the clinical data show that 1α,24(S)-dihydroxy vitamin $D_2$ significantly increases intestinal calcium absorption, as determined by direct measurements using a double-isotope technique. Patients treated with this compound show normalized serum calcium levels, stable values for total body calcium, and stable radial and spinal bone densities relative to baseline values. In contrast, patients treated with placebo show frequent hypocalcemia, significant reductions in total body calcium and radial and spinal bone density. An insignificant incidence of hypercalcemia is observed in the treated group.

EXAMPLE 15
Medicament Preparations.

A topical cream is prepared by dissolving 1.0 mg of 1α,24(S)-dihydroxy vitamin $D_2$ in 1 g of almond oil. To this solution is added 40 gm of mineral oil and 20 gm of self-emulsifying beeswax. The mixture is heated to liquify. After the addition of 40 ml hot water, the mixture is mixed well. The resulting cream contains approximately 10 μg of 1α,24(S)-dihydroxy vitamin $D_2$ per gram of cream.

EXAMPLE 16

An ointment is prepared by dissolving 1.0 mg of 1α,24 (S)-dihydroxy vitamin $D_2$ in 30 g of almond oil. To this solution is added 70 gm of white soft paraffin which had been warmed just enough to be liquified. The ointment is mixed well and allowed to cool. This ointment contains approximately 10 μg 1α,24(S)-dihydroxy vitamin $D_2$ per gram of ointment.

EXAMPLE 17

To the ointment of Example 14 is added with thorough mixing 0.5 g of adenosine and 2.0 g of papaverine base, both dissolved in a minimum quantity of dimethyl sulfoxide. The additional ingredients are present to the extent of about 0.5 wt % (adenosine) and 2 wt % (papaverine base).

EXAMPLE 18

To the ointment of Example 14 is added with thorough mixing 10,000 U of Vitamin A dissolved in a minimum quantity of vegetable oil. The resultant ointment contains about 100 U Vitamin A per gram of the ointment.

EXAMPLE 19

A dermatological lotion is prepared by dissolving 1.0 mg of 1α,24(S)-dihydroxy vitamin $D_2$ in 100 g of dry propylene glycol. The lotion is stored in a refrigerator in a brown bottle and contains about 10 μg of 1α,24(S)-dihydroxy vitamin $D_2$ per gram of lotion.

EXAMPLE 20

In 1 g of almond oil is dissolved 0.2 mg of 1α,24-dihydroxy vitamin $D_2$. To the solution is added 40 g of mineral oil and 20 g of self-emulsifying beeswax, followed by 40 ml of hot water. The mixture is mixed well to produce a cosmetic cream containing about 2.0 μg of 1α,24(S)-dihydroxy vitamin $D_2$ per gram of cream.

EXAMPLE 21

To a cosmetic cream prepared according to example 18 is added 100 mg adenosine. The cream is mixed well and contains about 0.1 wt % adenosine.

EXAMPLE 22

An ointment is prepared by dissolving 100 μg of 1α,24 (S)-dihydroxy vitamin $D_2$ in 30 g of almond oil. To the solution so produced is added 70 g white soft paraffin which had been warmed just enough to be liquified. The ointment is mixed well and allowed to cool. The ointment so produced contains about 1.0 μg of 1α,24-dihydroxy vitamin $D_2$ per gram of ointment.

EXAMPLE 23

To the cosmetic ointment of Example 18 is added with thorough mixing 200 U/g Vitamin A dissolved in a minimum amount of vegetable oil.

EXAMPLE 24

A cosmetic lotion is prepared by dissolving 300 μg of 1α,24-dihydroxy vitamin $D_2$ in 100 g of dry propylene glycol. The lotion is stored in a refrigerator in a brown bottle and contains about 3.0 μg 1α,24(S)-dihydroxy vitamin $D_2$ per gram of lotion.

EXAMPLE 25

Dermatological Testing.

Compositions containing 1α,24(S)-dihydroxy vitamin $D_2$ are evaluated for therapeutic efficacy of the composition in the topical treatment of dermatitis (contact and ectopic). The composition evaluated is an ointment containing 10 μg of 1α,24-dihydroxy vitamin $D_2$ per gram of ointment in a petrolatum-almond oil base. The control composition is identical except that it does not contain the active agent 1α,24(S)-dihydroxy vitamin $D_2$. The patients are treated in an out-patient clinic. They are instructed to use the preparation two times a day.

The ointment is as far as possible applied to a single lesion, or to an area of the disease. The ointment and its container are weighed before the treatment starts and returned with any unused contents for reweighing at the end of the treatment.

The area of the lesion treated is estimated and recorded, and the lesion is photographed as required, together with suitable "control" lesions. The latter are preferably lesions of similar size and stage of development, either in the vicinity of the treated lesion or symmetrically contralateral. Relevant details of the photographic procedure are recorded so as to be reproduced when the lesions are next photographed (distance, aperture, angle, background, etc.). The ointment is applied twice daily and preferably left uncovered. The "control" lesions are left untreated, but if this is not possible, the treatment used on them is noted.

Evaluations of erythema, scaling, and thickness are conducted at weekly intervals by a physician, with the severity of the lesion rated from 0 to 3. The final evaluation is usually carried out at the end of four to six weeks of treatment. Those lesions treated with 1α,24(S)-(OH)$_2$D$_2$ have lower scores than the control lesions. An insignificant incidence of hypercalcemia is also observed.

EXAMPLE 26

Epidermal Cell Differentiation and Proliferation Testing.

Human keratinocytes are cultured according to known modifications of the system originally described by Rheinwald and Green (*Cell*, vol. 6, p. 331 (1975)). The 1α,24(S)-dihydroxy vitamin $D_2$, dissolved in ethanol, is added to cells to yield a variety of concentrations between 0.05 and 5 μg/ml with the ethanol concentration not to exceed 0.5% v/v. Control cultures are supplemented with ethanol at a final concentration of 0.5% v/v.

Differentiation and proliferation of epidermal cells in culture is examined by:
1. quantitation of cornified envelopes;
2. quantitation of cell density of cells attached to disks;
3. monitoring transglutaminase activity; or
4. monitoring DNA synthesis by incorporation of $^3$H-thymidine.

Cultures incubated with 1α,24(S)-dihydroxy vitamin $D_2$ have more cornified envelopes, fewer attached cells, higher transglutaminase activity, and lower DNA synthesis than control cultures.

EXAMPLE 27

Activity of 1α,24(S)-(OH)$_2$D$_2$ in HL-60 Cell Differentiation Assay.

A dose-response study is conducted with 1α,24(S)-(OH)$_2$D$_2$ in the HL-60 cell differentiation assay as described by DeLuca and Ostrom (DeLuca, H. F. and Ostrem, V. K., *Prog. Clin. Biol. Res.*, vol. 259, pp. 41–55 (1988)). In this study, 1α,25-(OH)$_2$D$_3$ is used as a positive control and appropriate solvents are used as negative controls. The following variables are evaluated: nonspecific acid esterase activity, nitroblue tetrazolium (NBT) reduction, and thymidine incorporation. The results show that 1α,24(S)-(OH)$_2$D$_2$ has potent activity in promoting differentiation of HL-60 promyelocytes to monocytes.

EXAMPLE 28

Antiproliferative Activity of 1α,24(S)-(OH)$_2$D$_2$ in Human Cancer Cell Lines.

Dose-response studies are conducted with 1α,24(S)-(OH)$_2$D$_2$ in a battery of human cancer cell lines. These cell lines include, but are not limited to, the following: BCA-1 or ZR-75-1 (breast) and COL-1 (colon), as described by Shieh, H. L. et al. *Chem. Biol. Interact.*, vol. 81, pp. 35–55 (1982). In this study, appropriate solvents are used as negative controls. The results show that 1α,24(S)-(OH)$_2$D$_2$ has potent (and reversible) antiproliferative activity, as judged by inhibition of thymidine incorporation.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claims.

What is claimed is:

1. A method for treating breast cancer, comprising administering to a patient suffering therefrom an effective amount of 1α,24(S)-dihydroxyvitamin $D_2$ without causing hypercalcemia.

2. The method of claim 1, wherein said 1α,24(S)-dihydroxyvitamin $D_2$ is substantially free of its (R) stereoisomer.

3. The method of claim 1, wherein said amount is sufficient to inhibit abnormal proliferative activity of ZR-75-1 breast cancer cells.

4. A method of treating breast cancer, comprising administering to a patient suffering therefrom an effective amount of 1α,24(S)-dihydroxyvitamin $D_2$, wherein said amount is sufficient to inhibit abnormal proliferative activity of BCA-1 breast cancer cells without causing hypercalcemia.

5. The method of claim 4, wherein said 1α,24(S)-dihydroxyvitamin $D_2$ is substantially free of its (R) stereoisomer.

6. A method of inhibiting abnormal proliferative activity of human breast cancer cells, comprising treating the breast cancer cells with an effective amount of 1α,24(S)-dihydroxyvitamin $D_2$, sufficient to inhibit abnormal proliferative activity of the cancer cells.

7. The method of claim 6, wherein said treating step comprises contacting said cancer cells to 1α,24(S)-dihydroxy vitamin $D_2$.

8. The method of claim 6, wherein said breast cancer cells are BCA-1 or ZR-75-1.

9. The method of claim 6, wherein said 1α,24(S)-dihydroxyvitamin $D_2$ is substantially free of its (R) isomer, and said amount is sufficient to induce differentiation of said cancer cells.

10. The method of claim 6, wherein said 1α,24(S)-dihydroxyvitamin $D_2$ is formulated into a composition for use in local application wherein said effective amount of 1α,24(S)-dihydroxyvitamin $D_2$ is about 0.01 μg to 100 μg per gram of said composition.

* * * * *

UNITED STATES PATENT AND TRADEMARK OFFICE
CERTIFICATE OF CORRECTION

PATENT NO. : 6,166,000
DATED : December 26, 2000
INVENTOR(S) : Charles W. Bishop et al.

It is certified that error appears in the above-identified patent and that said Letters Patent is hereby corrected as shown below:

Title page,
Item [54], "METHODS FOR PREPARATION AND USE OF 1α, 24(S)-DIHYDROXY VITAMIN $D_2$" should read -- METHODS FOR PREPARATION AND USE OF 1α,24(S)-DIHYDROXY VITAMIN $D_2$ --.

Item [62] Related U.S. Application Data, please delete the current sentence and insert -- Division of application No. 08/275,641, Jul. 14, 1994, abandoned, which is a continuation of application No. 07/940,246, Aug. 28, 1992, abandoned, which is a continuation-in-part of application No. 07/637,867, Jan. 8, 1991, abandoned, and a 371 of application No. PCT/US 92/00313, Jan. 7, 1992, abandoned, which designated the U.S., and which is a continuation-in-part of application No. 07/637,867, Jan. 8, 1991, abandoned.

Item [56] References Cited, OTHER PUBLICATIONS, after reference "E. G. Bligh and W.J. Dyer, *Canadian Journal of Biochemistry and Physiology*, vol. 37, pp. 911-917 (1959)" please insert -- Harrison's Principles of Internal Medicine: Part Seven, "Disorders of Bone and Mineral Metabolism: Chap. 35," in E. Braunwald, K. J. Isselbacher, R. G. Petersdorf, J. D. Wilson, J. B. Martin and H. S. Fauci (eds.), *Calcium, Phosphorus and Bone Metabolism: Calcium Regulating Hormones*, McGraw-Hill, New York, pp. 1860-1865 --.

Column 1,
Line 10, after "U.S." please insert -- , and which is a continuation-in-part of application Ser. No. 07/637,867, filed Jan. 8, 1991, now abandoned. --.

Column 5,
Line 21, "hypothyroidism" should read -- hypoparathyroidism --.
Line 22, "pseudoparathyroidism" should read -- pseudohypoparathyroidism --.
Line 27, "1α,24(S)-Dihydroxy" should start a new paragraph.

Column 7,
Line 18, "AM-400(400MHz)" should read -- AM--400(400MHz) --.
Line 25, "1α,24(?)-$(OH)_2 D_2$" should read -- 1α,24(?)-$(OH)_2D_2$ --.

Column 8,
Line 32, "3.5" should read -- 3,5 --.
Line 32, "1.2" should read -- 1,2 --.

UNITED STATES PATENT AND TRADEMARK OFFICE
CERTIFICATE OF CORRECTION

PATENT NO. : 6,166,000
DATED : December 26, 2000
INVENTOR(S) : Charles W. Bishop et al.

It is certified that error appears in the above-identified patent and that said Letters Patent is hereby corrected as shown below:

Column 10,
Line 21, "tert-Butyl" should start a new paragraph.

Column 12,
Line 14, "Product" should read -- Production --.
Line 45, "µg/ml" should read -- pg/ml --.

Column 14,
Line 9, "2" and "µM" should be moved to line 6.

Column 18,
Line 27, the first "Ostrom" should read -- Ostrem --.

Signed and Sealed this

Eighteenth Day of December, 2001

*Attest:*

*Attesting Officer*

JAMES E. ROGAN
*Director of the United States Patent and Trademark Office*